United States Patent [19]

Goble et al.

[11] Patent Number: 5,013,316
[45] Date of Patent: May 7, 1991

[54] SOFT TISSUE ANCHOR SYSTEM

[76] Inventors: E. Marlowe Goble, 850 E. 1200 North; W. Karl Somers, 651 N. 150 West, both of Logan, Utah 84321

[21] Appl. No.: 498,831

[22] Filed: Mar. 26, 1990

[51] Int. Cl.$^5$ .................. A61F 5/04; A61F 2/08
[52] U.S. Cl. .................... 606/72; 606/75; 623/13
[58] Field of Search .............. 606/53, 54, 59, 65, 606/66, 67, 72, 73, 75, 104, 60; 623/13, 16; 411/389, 390, 490, 498

[56] References Cited

U.S. PATENT DOCUMENTS

| | | | |
|---|---|---|---|
| 446,871 | 2/1891 | Lieb | 411/389 |
| 1,617,818 | 2/1927 | Mackenzie | 411/490 |
| 2,381,050 | 8/1945 | Hardinge | 606/65 |
| 2,741,289 | 4/1956 | Grow | 411/389 |
| 3,103,926 | 9/1963 | Cochran | 606/104 |
| 3,133,378 | 5/1964 | Poupitch | 411/490 |
| 4,372,718 | 2/1983 | Zaydel | 411/389 |
| 4,632,100 | 12/1986 | Somers | 606/79 |
| 4,738,255 | 4/1988 | Goble | 623/13 |
| 4,772,286 | 9/1988 | Goble | 606/66 |
| 4,834,752 | 5/1989 | Van Kampen | 623/13 |
| 4,870,957 | 10/1989 | Goble | 623/13 |
| 4,878,915 | 11/1989 | Brantigan | 606/53 |

Primary Examiner—Robert A. Hafer
Assistant Examiner—Michael Brown
Attorney, Agent, or Firm—M. Reid Russell

[57] ABSTRACT

A soft tissue anchor involving a footing stud that includes a drill end followed by self tapping threads, the footing stud arranged for turning and tapping into a bone mass. The footing stud for endosteal seating at a ligament attachment site on that bone mass. A center longitudinal hole is arranged in that footing stud rear end that receives and locks to a pointed cone base end edge of a tack that is fitted therein. The tack includes a tack shaft whereto is axially attached, on one end, the pointed cone base with a broad head secured to the other shaft end. The tack broad head is disk shaped and includes spikes that project at spaced radial intervals from the undersurface thereof, parallel to the shaft, and includes a center axial threaded post that extends outwardly from a top surface thereof. Which threaded post is for turning into a threaded end of a tack driver. The tack pointed cone is for passing through a ligament, or the like, and locking in the footing stud, in which configuration the spikes that extend from the undersurface of the broad head spikes have penetrated the ligament and the ligament is held and compressed tightly against the bone surface.

8 Claims, 2 Drawing Sheets

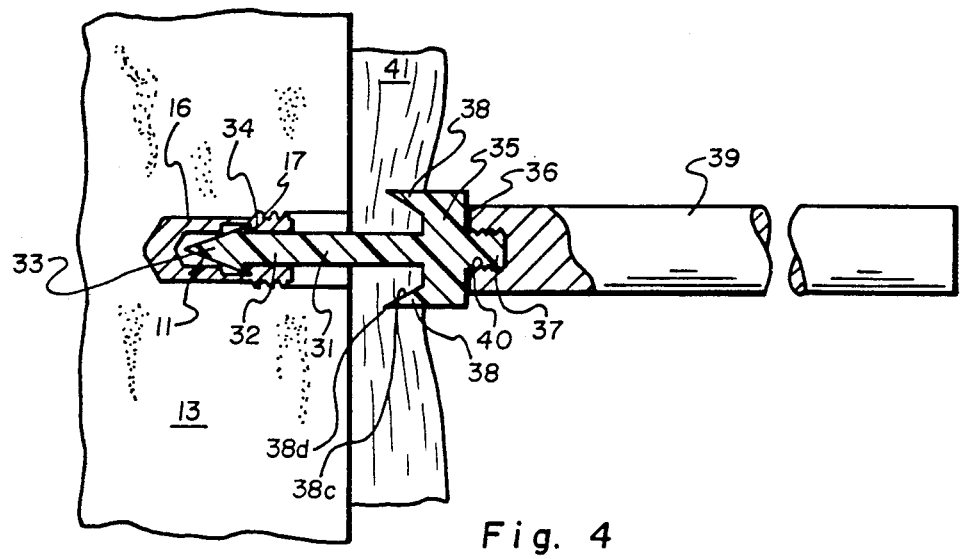
Fig. 4
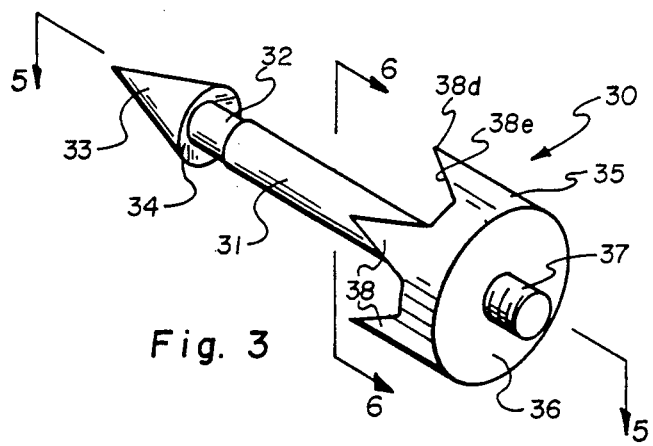
Fig. 3
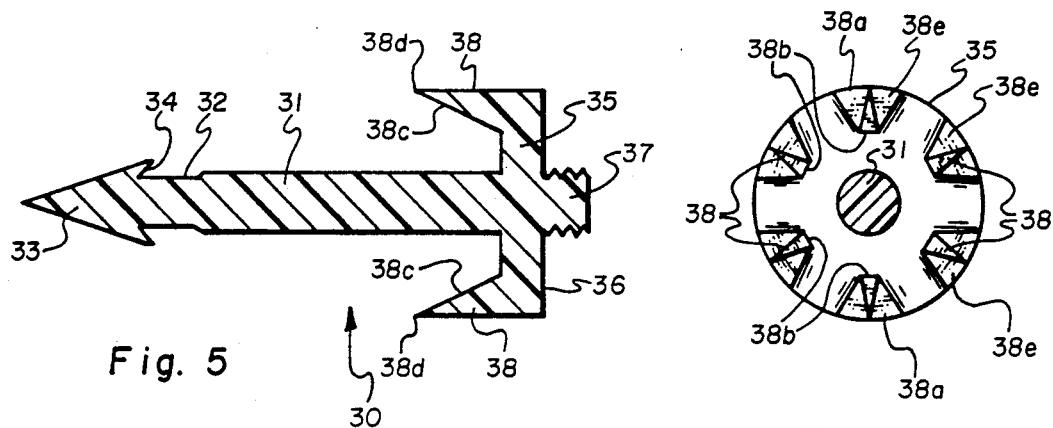
Fig. 5
Fig. 6

SOFT TISSUE ANCHOR SYSTEM

BACKGROUND OF THE INVENTION

1. Field of the Invention

The present invention relates to devices used in ligament repair and replacement surgery and particularly for devices for securing a ligament onto a bone surface.

2. Prior Art

Heretofore a number of devices and tools have been developed for securing a ligament to or endosteal within a bone mass in a practice of ligament repair and replacement surgery. Such devices include staple and staple like devices and tooling therefore that have been utilized for securing a ligament to a bone surface. Such staple devices are usually "U" or channel shaped, having parallel legs, the ends of which are to be driven into a bone surface, with a web area between the parallel legs to sandwich a ligament against the bone surface. For example, such devices are shown in: U.S. Pat. No. 4,592,346 to Jurgutis; U.S. Pat. No. 4,278,091 to Borzone; U.S. Pat. No. 4,793,335 to Freg, et al.; U.S. Pat. No. 4,047,524 to Hall; U.S. Pat. No. 4,146,022 to Johnson, et al.; U.S. Pat. No. 4,414,967 to Shapiro; and U.S. Pat. No. 4,400,833 and U.S. Pat. Nos. 4,263,903 and 4,438,769 to Griggs and Pratt, et al., respectively. Which staples or channels, or drivers therefore are obviously not like the present invention.

Additional to staples and channel type clamping devices, retention posts or pins have also been employed for coupling a ligament onto a bone mass. For example, U.S. Pat. No. 4,711,234 to Vives, et al., U.S. Pat. No. 4,759,765 to VanKampen, and U.S. Pat. No. 4,590,928 to Hunt, et al. all show pins for fitting through a ligament that have expanding shank ends for fitting into a pre-formed hole in a bone mass so as to lock the ligament onto the bone mass surface.

Also the present inventors have themselves developed ligament anchoring devices, as set out in U.S. Pat. Nos. 4,632,100 and 4,772,286, and in U.S. patent application Serial No. 235,194, entitled "Channel Ligament Clamp and System", and the inventor E. Marlowe Goble is joint inventor of still another ligament anchor system, U.S. Pat. No. 4,738,255. Which U.S. Pat. No. 4,772,286 relates to an expanding head for a ligament end, and U.S. patent application Serial No. 235,194, that relates to a channel clamp. These devices are not tack fasteners like the present invention and accordingly unlike the present invention.

Like the above set out U.S. Pat. Nos. 4,632,100 and 4,738,255, the present invention utilizes a stud that is endosteally installed in a bone mass. Distinct therefrom, however, the present invention utilizes a tack rather than provides a suture for attaching a ligament to the stud, as shown in these stud patents. Rather, the present invention utilizes a stud for seating in a bone mass as a footing only. The footing is for receiving and locking to a pointed end of a tack whose head end includes spikes. Which spikes extend from the head undersurface to penetrate a ligament, clamping the ligament onto the bone mass surface.

BRIEF SUMMARY OF THE INVENTION

It is a principal object of the present invention in a soft tissue anchor to provide a system of a footing and tack for attaching and clamping a ligament onto a bone mass.

Another object of the present invention is to provide a self tapping stud for turning and endosteal seating into a bone mass utilizing a driver, which stud is internally configured to receive and lock to a pointed end of the tack.

Another object of the present invention is to provide a tack having a cone shaped pointed end, the cone having a forward sloping base and edge for binding in an internal groove of the stud, which tack further includes a broad head end wherefrom the undersurface of which project spikes that are for engaging and penetrating into a ligament.

Still another object of the present invention is to provide a post, as a right angle extension from the tack head top surface, that is for coupling to a driver end.

Still another object of the present invention is to provide a stud and tack that are suitable for human implantation.

In accordance with the above objects, the present invention is in a system of a footing stud and tack that are for human implantation to secure a ligament onto a bone surface. The footing stud is arranged for turning with a driver into a bone mass. The stud has a cylindrical body that includes a drill end. The drill end includes flutes that extend back along the body to intersect a number of flights of self tapping threads, which threads continue to the cylindrical body rear end. The cylindrical body rear end is holed longitudinally, which hole is stepped outwardly at the cylinder mid-section. A rear face of which stepped portion, opposite to the stud rear end is slopped rearwardly, forming a groove, and the rear end of which hole is sided for engaging the sides of an end of a driver that is for fitting therein for turning the footing stud.

The driver, from the sided end is stepped outwardly at a first shoulder into a cylindrical section that has approximately the same diameter as does the stud cylindrical body. This first driver section from the first shoulder is to follow the footing stud into a hole it drills into a bone mass. The driver body is again stepped outwardly from the first section into a second shoulder, which second shoulder forms a forward wall that is to block further penetration of the driver into the formed hole. So arranged, the footing stud endosteal depth of penetration into a bone mass is set by the length of the driver first section that is the spacing distance between the driver end and the second shoulder forward wall.

The footing stud, when set endosteally at a desired depth into a bone mass, is ready to receive a pointed cone shaped end of a tack urged therein. Which pointed cone base slopes inwardly from the cone base ends to intersect a straight shaft of the tack, the other shaft end at a right angle to the undersurface of a broad head. Which broad head includes, a threaded post that extends axially from the flat top surface of that broad head. Which broad head undersurface includes spaced apart spikes projecting at radial points from the undersurface thereof. Which spikes are essentially parallel to the shaft and point in the same direction as the cone pointed end.

A driver that has a tapped center longitudinal hole formed in one end thereof is provided for urging the tack cone end into the implanted footing stud. The tack broad head threaded post that extends axially at a right angle from that broad head flat surface is for turning in the driver holed and tapped end, mounting the tack as an extension to the driver end.

In practice, the footing stud is turned into at bone mass at the site of a ligament end attachment point. With the second shoulder forward wall of the stud driver stopping further driver penetration setting the endosteal depth of that footing stud in the bone mass. With the footing stud in place, a surgeon, with one hand, maintains a section of a ligament over the footing stud end. In his other hand he holds the tack driver mounting a tack to the end thereof and urges the tack pointed cone end through the ligament and into the stud end. The pointed cone end of which tack shaft will pass into that footing stud until the edge of the cone base is forced into the footing stud mid-section. Which cone base edge is of greater diameter that the entry into which footing stud mid-section, and flexes inwardly to pass thereby. Once inside that mid-section the cone returns to its original diameter and locks into the slopped groove end of that footing stud mid-section, permanently coupling the tack cone end in that footing stud.

As the tack cone end travels into the footing stud, the spikes that extend from the tack broad head undersurface penetrate into the ligament. Additional points of engagement of the tack to the ligament are thereby provided to that provided by the tack shaft. The ligament is thereby compressed by the tack head and spikes against the bone surface. The tack driver can then be turned off of the tack, leaving the footing stud and tack in place. So arranged, the ligament will grow to the bone surface during the healing process.

The tack and footing stud are preferably constructed of a material to be suitable for remaining in the body after healing is complete and may be biodegradable within the scope of this disclosure.

DESCRIPTION OF THE DRAWINGS

These and other objects and features of the present invention will become more fully apparent from the following description taken in conjunction with the accompanying drawings.

FIG. 3 is a profile perspective view of a tack of the present invention;

FIG. 4 is a side elevation sectional view showing the bone with the footing stud of FIG. 1 endosteally seated therein, with the footing stud shown implanted in the bone mass, and with the tack of FIG. 3, shown mounted to the end of a driver, and fitted into that footing stud and showing a section of a ligament maintained beneath a head of which tack and compressed against the bone surface;

FIG. 5 is a longitudinal sectional view taken along the line 5—5 of FIG. 3; and

FIG. 6 is a sectional view of the undersurface of the tack broad head end taken along the line 6—6 of FIG. 3.

DETAILED DESCRIPTION

Figure 1:
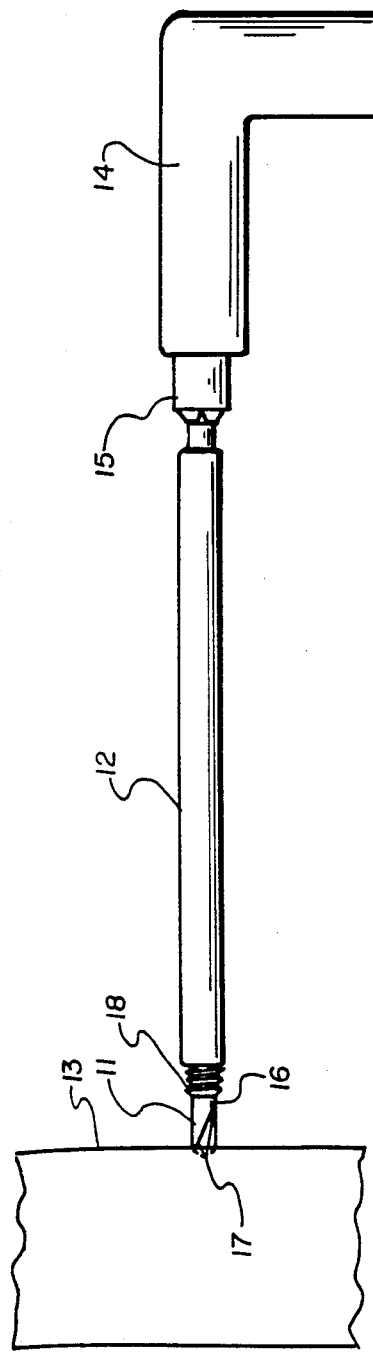
FIG. 1 is a side elevation sectional view of a section of bone with a footing stud of the invention shown being turned through a driver by a drill that is operated by a surgeon, not shown.

The present invention is in a soft tissue anchor system for anchoring a ligament, tendon, or like graft onto a bone surface. The system is particularly useful where access to the bone surface whereto the ligament is to be attached is limited, such as could be the case in an arthroscopic surgical procedure. In such procedure for attaching a ligament to a certain or optimum location on a bone surface, as shown in FIG. 1, a surgeon can position an end of a footing stud 11, that is mounted to the end of a driver 12, onto a point or location on a bone surface 13. The opposite driver end is preferably mounted in a chuck 15 of a turning device or appliance, shown as a drill 14. A surgeon, not shown, holding the drill 14 can conveniently position a footing stud 11 drill end 17 onto a certain location on a bone surface where a ligament is to be attached. They can then operate the drill to turn the footing stud 11 into the bone 13 to a desired depth, as set out below.

Figure 2:
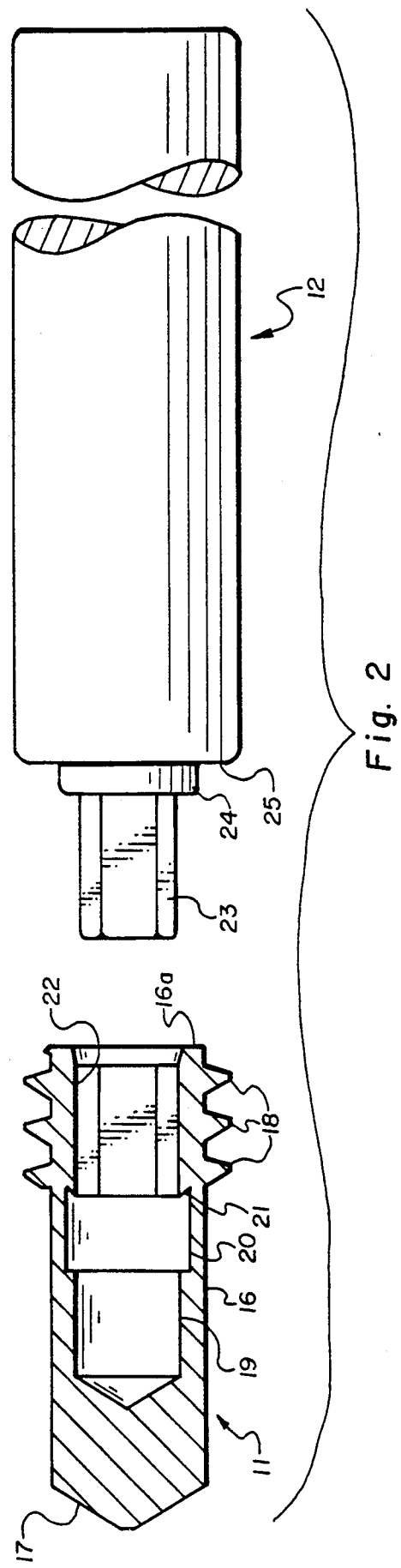
FIG. 2 is an expanded side elevation exploded view of the footing stud, shown as a longitudinal section, and a section of a forward portion of the driver of FIG. 1.

FIG. 2 shows, as an exploded view, a longitudinal section of the footing stud 11, that is aligned to receive the driver 12. Shown in FIGS. 1, 2 and 4, the footing stud 11 has a cylindrical body 16 and includes a pointed drill end 17, that is preferably a fluted drill and extends, as the footing stud forward portion, to approximately a mid-point, wherefrom several flights of threads 18 are formed to the cylinder rear end. Which threads 18 are arranged for tapping and turning through a bone cortex, so as to seat within the bone mass. The footing stud drill end and threads are similar to the arrangements shown in an earlier patent of the present inventors, U.S. Pat. No. 4,632,100.

The footing stud cylindrical body 16 is holed longitudinally at 19 from a rear end 16a, terminating within the body near the drill end. The hole 19 is stepped outwardly into a center section 20 that is at a mid-area of which cylinder. Which center section 20 includes a rear facing notch or groove 21 formed therein around the rear most edge. Rearwardly from which notch or groove 21 to the footing stud rear end 16a the hole 19 is shown as sided at 22 for receiving a like sided end shaft 23 of driver 12 for fitting therein. Which driver 12 is for turning the footing stud, as illustrated in FIG. 1. Preferably, the sided portion 22 of hole 19 and sided end shaft 23 of driver 12 have hexagonal cross-sections. The relationship of footing stud 11 with hole 19 and the center and sided sections 20 and 22, will be discussed hereinbelow in relation to a functioning thereof with a tack 30 of the present invention.

Shown best in FIG. 2, the driver 12 is preferably cylindrical and is stepped outwardly as a first shoulder 24 back from the forward sided shaft end 23. First shoulder 24 is shown as having approximately the same or slightly smaller diameter as does the footing stud cylindrical body that is the diameter of its drill end, the driver first shoulder 24 to follow the footing stud into a hole formed by that footing stud being turned into a bone, as shown in FIG. 4. Shown in FIG. 4, the footing stud rear end 16a is set endosteal a distance into bone 13 that is the length of driver first shoulder 24.

Shown in FIG. 2, the driver 12, from a rear end of first shoulder 24 is stepped at a right angle into a wall 25. Wall 25 terminates in the driver 12 body that extends therefrom to a coupling end for fitting in chuck 15 of drill 14, as shown in FIG. 1. The driver wall 25 has a greater diameter than does the footing stud 11 and accordingly will contact the bone 13, around the hole drilled therein by footing stud 11, prohibiting further travel of which footing stud 11 and driver sided end 23 into that bone mass. Which optimum depth of footing stud endosteal penetration relates to the configuration of tack 30, as set out hereinbelow, and as illustrated in FIG. 4. Additionally to preclude the footing stud 11 from falling off of the sided end 23 of the driver 12 during installation, the footing stud 11 can include a suture mounted loosely within the footing stud longitudinal hole (not shown). The suture extending back through a longitudinal passage, (not shown), through the driver. The suture-footing stud combination is like the "Suture Anchor Assembly" shown in U.S. Pat. No. 4,632,100 of the present inventors except it is mounted to be removable as by knotting the suture end that is forced into the footing stud end, or by mounting it onto a disk that is installed in the footing stud 11 longitudinal hole 19, or like a mounting, not shown, can be utilized. So arranged, after the footing stud is turned into a bone, a surgeon pulling thereon can force the suture that is then pulled from the footing stud with the removal of the driver. Which suture is for maintaining the footing stud on the driver end during installation only.

FIG. 3 shows a profile perspective view of a preferred embodiment of a tack 30 of the system of the present invention. Tack 30 consists a cylindrical shaft 31 that is of uniform diameter to a forward portion 32 that is slightly necked down. A base 34 of a pointed cone 33 is shown axially attached to the cylindrical shaft at the end of the necked down forward portion 32. Cone base 34 is shown as sloped from its outer edge inwardly towards the cone pointed end intersecting the tack shaft at the necked portion 32. This arrangement, as shown best in FIG. 5, provides a cone base edge that is capable of flexing inwardly, toward the shaft necked portion, and will spring outwardly when a compressive force is exerted thereon in passing into the footing stud from the sided section 22 into the center section 20, providing locking within the footing stud 11 of the cone base 24 edge in the notch or groove 21.

Shown in FIGS. 3 through 6, a broad head 35 is axially secured to the end of cylindrical shaft 31, opposite to the pointed cone 33. A top surface 36 of which broad head 35 is shown as flat and includes a threaded post 37 that extends axially, at a right angle, from the center thereof. Which threaded post 37 is for turning into a threaded end hole 40 of a tack driver 39, as shown best in FIG. 4.

Shown in FIGS. 3 through 6, an undersurface of tack broad head 35 includes a number of equidistant radially spaced apart spikes 38 that individually project rearwardly, and are approximately parallel to one another and to the shaft 31. Shown in FIG. 6, the spikes 38 are pointed to penetrate into a ligament 41, tendon, or like graft, further securing it to the surface of bone 13. Accordingly, to prohibit canting or bending of spikes 38 should a lateral force or forces be applied to the ligament 41 as could disrupt the ligament to bone contact during healing, the spikes are preferably formed to have a wide base. Shown best in FIG. 6, each spike base has two sides that taper together radially from a wide arcuate side 38a that is the broad head circumference, tapering into a flat lateral side 38b. Which lateral side 38b also tapers upwardly and outwardly as a hypotenuse side 38c to a pointed end 38d, as shown best in FIG. 5. Each spike 38 is also shown in FIG. 6 to taper upwardly and inwardly as sides 38e, that extend from the base radial sides to the point 38d, shown in FIGS. 3 and 5. So arranged, the spike 38 is formed to have a wide base at the undersurface of broad head 35, and tapers inwardly from both its radial and lateral sides, into the spike pointed end 38d, forming, essentially half pyramidal segments. Each spike 38 is therefore rigid and resists side to side bending or flexure.

In practice, for securing a ligament, tendon, or like graft, hereinafter referred to as ligament 41, to a bone 13 surface, the footing stud 11 mounted to driver 12 end 23 is positioned on and turned into bone 13. The footing stud is turned into the bone mass 13 to a desired depth as governed by the length of the driver 12 first shoulder 24. With the footing stud 11, as shown in FIG. 4, seated endosteally and the driver 12 removed, that footing stud is ready to receive and permanently couple to tack 30.

Shown in FIG. 4, with the footing stud 11 seated at a desired distance endosteally to the bone surface 13, a surgeon, not shown, positions a ligament 41 over the footing stud 11 end 16a within the bone. Holding the ligament in that position, the surgeon, with his other hand, aligns the tack driver 39, that has the tack 30 threaded post 37 turned into the tapped hole 40 in the end thereof, with the opening in the footing stud end 16a and forces the tack pointed cone 33 through the ligament and into that hole. The tack 30 is urged into and along the footing stud longitudinal hole 19 with the pointed cone edge collapsing and traveling through the sided portion 22 and into the center portion 20. The edge of the cone base 24 thereby collapses towards the tack necked down portion 32 as the tack pointed cone end continues along hole 19, with the cone base stationed in the footing stud center section 20, the sloping notch or groove 21 will receive and lock to the cone base edge that has flexed outwardly to its full diameter within that center section. So arranged, the cone pointed end will rest in the end of hole 19, as shown best in FIG. 4. Thereafter, an attempt to pull the tack pointed cone end 33 out of the footing seat will seat and lock the cone base edge in that sloping notch or groove 21 of the footing stud center section 20.

With the tack 30 cone end 33 seated as described, the ends 38d of spikes 38 will be a distance above the bone surface, as illustrated in FIG. 4. Which distance is governed by the depth of the footing stud 11 in the bone 13 and length of tack shaft 31. This spacing is selected to provide for a penetration of the ligament 41 with each spike 38 to just above the bone surface 13, pinching the ligament tightly against that bone surface. The combination of the tack broad head 35 undersurface with spikes 38 and the shaft 31 fitted through the ligament prohibit movement of that ligament on the bone surface, encouraging healing of that ligament to that bone surface.

As set out above, the footing stud 11 is for seating in bone 13 and accordingly needs to be manufactured from a material that is suitable for human implantation. A stainless steel is such a material. However, it should be understood that the footing stud and the tack can be manufactured from another material that is suitable for the use described above, within the scope of this disclosure. As to the tack 30, as the base of its pointed cone end 33 needs to be flexible so as to collapse its base edge to pass into the footing stud center section 20, which edge to expand into sloping notch or groove 21, that tack needs to be manufactured from a somewhat resilient or flexible material such as a plastic. Which plastic can be biodegradable, such as DELRIN®, or a like material, within the scope of this disclosure.

While a preferred embodiment of the invention in a soft tissue anchor system has been shown and described herein, it should be understood that the present disclosure is made by way of example only and that variations to the structure shown and its use are possible within the scope of this disclosure without departing from the subject matter coming within the scope of the following claims, and a reasonable equivalency thereof, which claims we regard as our invention.

We claim:

1. A soft tissue anchor system comprising, a footing stud means for endosteal installation in a bone mass at a site of a soft tissue attachment that includes a longitudinal cavity for receiving a tack which has a central portion that has a greater diameter than distal and proximal ends of said cavity a cone axially secured to the tack means shaft end by attaching the shaft into a cone base central portion of said longitudinal cavity formed in said footing stud means, allowing said cone to collapse towards said tack means shaft and, when released, expand into said footing stud central portion for permanently coupling said tack means to said footing stud means, with a head axially secured to the other tack means shaft end.

2. A soft tissue anchor system as recited in claim 1, further including a driver for releasable coupling to the footing stud means to turn it into the bone mass; and means for limiting driver penetration into said bone mass at a certain depth of said footing stud means.

3. A soft tissue anchor system as recited in claim 2, wherein the driver includes a sided coupling end for fitting into a like sided end hole formed into the footing stud; and the means for limiting driver penetration is a forward wall of a stepped portion of said driver.

4. A soft tissue anchor system as recited in claim 1, wherein the footing stud means is cylindrical and includes a drill on one end with several flights of threads formed on a cylindrical surface from approximately a mid-point to a cylinder rear end.

5. A soft tissue anchor system as recited in claim 4, wherein the center hole in said footing stud includes a groove that is formed therein that is of greater diameter than said central portion and is for receiving said tack means cone base edge therein.

6. A soft tissue anchor system as recited in claim 1, wherein the tack means head is disk shaped and includes spike means that extend from an undersurface thereof alongside, and essentially parallel to the tack means shaft, said spike means for engaging and penetrating a soft tissue surface wherein the tack means shaft has passed.

7. A soft tissue anchor as recited in claim 6, wherein the spike means are individual pointed spikes that extend at spaced radial increments from the head undersurface.

8. A soft tissue anchor as recited in claim 6, further including a threaded post that extends outwardly from the center of the tack means disk shaped head top surface at a right angle thereto; and a tack means driver means that includes a tapped longitudinal hole formed in one end suitable for turning onto said threaded post.

* * * * *